US010232105B2

(12) United States Patent
Tenreiro et al.

(10) Patent No.: US 10,232,105 B2
(45) Date of Patent: Mar. 19, 2019

(54) MULTI-CHAMBER MICROFLUIDIC DEVICE

(75) Inventors: Tânia Tenreiro, Lisbon (PT); Nuno Reis, Almargem do Bispo (PT); João Garcia Da Fonseca, Azambuja (PT)

(73) Assignee: Biosurfit, S.A., Aveiro (PT)

(*) Notice: Subject to any disclaimer, the term of this patent is extended or adjusted under 35 U.S.C. 154(b) by 156 days.

(21) Appl. No.: 14/007,812

(22) PCT Filed: Mar. 28, 2012

(86) PCT No.: PCT/IB2012/051490
§ 371 (c)(1),
(2), (4) Date: Dec. 3, 2013

(87) PCT Pub. No.: WO2012/131598
PCT Pub. Date: Oct. 4, 2012

(65) Prior Publication Data
US 2014/0087934 A1 Mar. 27, 2014

(30) Foreign Application Priority Data
Mar. 28, 2011 (PT) .......................... 105589

(51) Int. Cl.
A61M 1/36 (2006.01)
B01L 3/00 (2006.01)
B04B 5/04 (2006.01)

(52) U.S. Cl.
CPC ....... *A61M 1/3693* (2013.01); *B01L 3/50273* (2013.01); *B01L 2200/0621* (2013.01);
(Continued)

(58) Field of Classification Search
CPC ............. A61M 1/3693; B01L 3/50273; B01L 2200/0621; B01L 2200/10;
(Continued)

(56) References Cited

U.S. PATENT DOCUMENTS 6,143,248 A * 11/2000 Kellogg ............. B01F 13/0059
422/503
6,235,531 B1  5/2001 Kopf-Sill et al.
(Continued)

FOREIGN PATENT DOCUMENTS

CA      2925839 A1    4/2015
DE  102013203293 A1   8/2014
(Continued)

OTHER PUBLICATIONS

Search Report dated Nov. 7, 2016 for Portuguese Application No. 109453, 6 pages.
(Continued)

*Primary Examiner* — Walter D. Griffin
*Assistant Examiner* — Shuyi S Liu
(74) *Attorney, Agent, or Firm* — Patterson Thuente Pedersen, P.A.

(57) ABSTRACT

A liquid handling device having an upstream liquid handling structure connected to a downstream liquid handling structure by a conduit. The upstream and downstream liquid handling structures are sealed or sealable such that the conduit provides the only fluidic communication paths between the upstream and downstream liquid handling structure. The device is arranged such that a driving force causes liquid in the upstream liquid handling structure to at least partially fill the conduit to separate gas in the upstream liquid handling structure from gas in the downstream liquid handling structure. With the device set up such that the two gas volumes are separated by a liquid volume, gas pressures and liquid flow in the device can be controlled by control of the driving force. The device may be arranged for rotation about an axis of rotation to provide the driving force.

5 Claims, 8 Drawing Sheets

(52) U.S. Cl.
CPC ..... *B01L 2200/10* (2013.01); *B01L 2300/087* (2013.01); *B01L 2300/14* (2013.01); *B01L 2400/0409* (2013.01); *B01L 2400/0688* (2013.01); *B01L 2400/0694* (2013.01); *B04B 5/0407* (2013.01)

(58) Field of Classification Search
CPC .......... B01L 2300/087; B01L 2300/14; B01L 2400/0409; B01L 2400/0688; B01L 2400/0694; B04B 5/0407
USPC ....................................... 494/9, 37
See application file for complete search history.

(56) References Cited

U.S. PATENT DOCUMENTS

| | | | | |
|---|---|---|---|---|
| 7,575,681 | B2* | 8/2009 | Angelescu | B01D 17/085 166/308.3 |
| 8,221,701 | B2 | 7/2012 | Cho et al. | |
| 2005/0199500 | A1 | 9/2005 | Gason et al. | |
| 2008/0017634 | A1 | 1/2008 | Wiezoreck et al. | |
| 2008/0110500 | A1* | 5/2008 | Kido | B01L 3/502723 137/8 |
| 2008/0237151 | A1* | 10/2008 | Cho | B01L 3/502738 210/781 |
| 2008/0317634 | A1* | 12/2008 | Kido | B01L 3/502715 422/72 |
| 2009/0035847 | A1* | 2/2009 | Cho | B01F 11/0002 435/289.1 |
| 2009/0053108 | A1 | 2/2009 | Cho et al. | |
| 2009/0209752 | A1 | 8/2009 | Peters et al. | |
| 2009/0317896 | A1* | 12/2009 | Yoo | B01L 3/502738 435/287.1 |
| 2010/0021347 | A1* | 1/2010 | Garcia Da Fonseca | B01L 3/50273 422/82.05 |
| 2010/0175994 | A1* | 7/2010 | Lee | B01L 3/502753 204/416 |
| 2018/0280969 | A1 | 10/2018 | Tenreiro et al. | |

FOREIGN PATENT DOCUMENTS

| | | | | |
|---|---|---|---|---|
| EP | 1 459 795 A1 | | 9/2004 | |
| EP | 1459795 A1 | * | 9/2004 | ........ B01L 3/502738 |
| EP | 1980322 A1 | * | 10/2008 | ........ B01L 3/502738 |
| JP | 2001503854 A | | 3/2001 | |
| KR | 20080022035 A | * | 3/2008 | .......... B01F 11/0002 |
| KR | 20100083029 A | * | 7/2010 | ........ B01L 3/502753 |
| WO | WO 98/07019 | | 2/1998 | |
| WO | WO 2010047609 A1 | * | 4/2010 | .......... G01N 33/491 |
| WO | WO 2013/124258 A1 | | 8/2013 | |

OTHER PUBLICATIONS

Robert Gorkin III et al., "Pneumatic pumping in centrifugal microfluidic platforms", Feb. 17, 2010, 9 pages.
Steffen Zehnle et al., "Microfluidic Centrifugo-Pneumatic Siphon Enables Fast Blood Plasma Extraction With High Yield and Purity", 16th International Conference on Miniaturized Systems for Chemistry and Life Sciences, Oct. 28-Nov. 1, 2012, Okinawa, Japan, 3 pages.
Search Report and Written Opinion dated May 12, 2017 for PCT Application No. PCT/EP2016/081320, 26 pages.
Search Report dated May 27, 2011 for Portuguese Application No. 105589, 6 pages.
Office Action dated Sep. 6, 2018 for EP Application No. 12716631.2, 5 pages.
Application and File history for U.S. Appl. No. 15/532,083, filed Dec. 15, 2016. Inventors: Tenreiro et al.

* cited by examiner

MULTI-CHAMBER MICROFLUIDIC DEVICE

PRIORITY CLAIM

This application is a National Phase entry of PCT Application No. PCT/IB2012/051490, filed Mar. 28, 2012, which claims priority from Portugal Application No. 105589, filed Mar. 28, 2011, the disclosures of which are hereby incorporated by referenced herein in their entirety.

TECHNICAL FIELD OF THE INVENTION

The present invention relates to processes, systems and devices for handling liquids, in particular but not exclusively fluid switching, fluid dosing, pumping and other fluidic functions. More particularly, although not exclusively, the present invention relates to microfluidic devices, such as centrifugal microfluidic devices.

BACKGROUND OF THE INVENTION

For various analytic systems and processes it is necessary to perform liquid switching functions, such as switching flow of liquids on and off in pre-defined and controlled ways. These switching functions are typically performed by active valves in the analytic system, using in some cases moving parts and typically involving hardware and controlling elements that add to the complexity of the analytic system. In a similar manner, various analytic systems use liquid dosing functions for different tasks, namely sample or reagent dispensing, aliquoting, mixing, etc. Again, conventional analytic systems incorporate dosing elements having active components having either mechanical moving parts or electrical elements, controllers, hardware and other complex sub-systems that add to system complexity and cost. Furthermore, other fluidic functions are sometimes required (such as fluid pumping, mixing, etc) requiring further complex processes and active elements in conventional systems.

Therefore, in order to simplify analytical tasks, processes and systems, it would be useful to be able to use analytic systems and devices having enhanced fluid switching, fluid dosing and/or other fluidic functions without the need for active elements or external control components.

SUMMARY OF THE INVENTION

Aspects of the invention are set out in the independent claims. Further, optional features of embodiments of the invention are set out in the dependent claims.

In some embodiments, a device for handling liquid comprises an upstream liquid handling structure, a downstream liquid handling structure and a conduit connecting the upstream liquid handling structure to the downstream liquid handling structure. The conduit enables liquid to flow from the upstream liquid handling structure to the downstream liquid handling structure in response to a driving force. The upstream and downstream liquid handling structures are sealed or sealable such that the conduit provides the only fluidic communication path between the upstream liquid handling structure and the downstream liquid handling structure. The device is arranged such that a driving force causes liquid in the upstream liquid handling structure to at least partially fill the conduit to separate gas in the upstream liquid handling structure from gas in the downstream liquid handling structure.

By providing a liquid handling structure which can separate two volumes of gas by an intermediate volume of liquid, without any other fluidic communication paths between the gas volumes, the pressure in one or both of the gas volumes can be controlled by application of the driving force to cause liquid flow from the upstream liquid handling structure towards the downstream liquid handling structure. This exploits the fact that changes in the gas volume in the upstream and/or downstream liquid handling structure as liquid flows causes corresponding pressure changes. Likewise, since the resulting pressure differentials need to be balanced by the driving force, the pressure changes can be used to control flow behaviour as described below in more detail.

The liquid handling structures may include any structure suitable for handling liquid, for example, without limitation, one or more of a channel, a chamber, or a combination of one or more of these.

In some embodiments, the device is arranged for rotation about an axis of rotation to provide the driving force and the upstream liquid handling structure comprises a liquid holding chamber. The liquid holding chamber may have an outlet port with the conduit extending radially outward of the outlet port. In some embodiments, the conduit extends radially outward from the outlet port.

In some embodiments, the liquid holding chamber has a portion extending radially outward of the outlet port. By providing a portion of the liquid holding chamber which extends radially outward of the outlet port, a phase separation chamber is provided in which a heavier phase of a liquid in the liquid handling structure can sediment into the radially outward extending portion so that only a lighter phase of the liquid can flow through the conduit. This structure can be used for material separation by spinning the device at a rotational frequency at which a gas pressure difference between the upstream and downstream liquid handling structures retains liquid in the liquid holding chamber against the centrifugal force to allow a heavier phase to sediment out.

With a subsequent increase of the centrifugal force to overcome the pressure difference, the lighter phase can then be made to flow to the downstream liquid handling structure, for example for further processing in the device. The downstream liquid handling structure may comprise a liquid receiving chamber that has an outlet port adjacent a liquid receiving zone for receiving liquid from the upstream liquid handling structure. The liquid receiving zone may extend radially outward of the outlet port of the liquid receiving chamber to provide another trap for preventing heavier components of the heavier phase of the liquid that may have flowed from the upstream liquid handling structure from flowing further downstream.

In some embodiments, the liquid holding chamber has a circumferential extent which is larger than its radial extent. This means that the liquid in the liquid holding chamber will be distributed predominately circumferentially so that the change in liquid head of the liquid for a given volume of liquid dispensed from the liquid holding chamber is smaller than would be the case if the radial extent of the liquid holding chamber was greater than the circumferential extent. The relatively small change in the liquid head as liquid is dispensed means that the change in the balance of centrifugal forces and induced gas pressures, as liquid is dispensed, is smaller. This makes the device easier to control. Similarly, the conduit may have a radial extent larger than a radial extent between the outlet port of the liquid holding chamber and a fill level of the liquid holding chamber. Again, by arranging the liquid head experienced by the liquid to be located predominately in the conduit (which remains filled until nearly all liquid has been dispensed) percentage changes in liquid head as liquid is dispensed are again kept low.

In some embodiments, the liquid holding chamber has a port connected to another portion of the upstream liquid handling structure for reducing the gas pressure in the other portion of the liquid handling structure as liquid flows through the conduit. Additionally, or alternatively, in some embodiments the downstream liquid handling structure has a liquid holding chamber having a port connected to another portion of the downstream liquid handling structure for increasing the gas pressure in the other portion when liquid flows through the conduit. In these embodiments, the gas pressure changes induced by the liquid flow are used as a pressure source, for example to control flow behaviour in other parts of the device. For example, a pressure reduction or increase can be used to pump or dose liquids in other parts of the device.

In some embodiments, the conduit is arranged to fill with liquid across its full cross section as soon as it is contacted by liquid, thereby ensuring an efficient seal between the two gas volumes as soon as possible. Of course, it will be understood that it is sufficient for the liquid to separate the two gas volumes at some stage for operation of the device as described above.

In some embodiments there is provided a system for controlling liquid flow in a device as described above. The system comprises a controller for controlling an amplitude of the driving force. The controller is arranged to vary the driving force between an upper and a lower limit to repeatedly dispense liquid through the conduit to the downstream liquid handling structure.

The controller may be arranged to periodically vary the driving force to repeatedly dispense the liquid through the conduit, for example repeatedly increasing the driving force above a threshold to dispense liquid through the conduit and, subsequently, decreasing the driving force below a threshold to equilibrate gas pressures in the upstream and downstream liquid handling structures.

In some embodiments, the system comprises a motor for rotating the device about an axis of rotation under control of the controller.

In some embodiments the controller is arranged to apply the driving force at a level below the lower limit prior to dispensing the liquid, to separate the liquid into fractions before it is dispensed. Subsequently, when the liquid is dispensed, a denser fraction of the liquid is retained in the upstream liquid handling structure. For example, the liquid may include a blood sample and the separated and retained denser fraction may then comprise cellular material of the blood sample with blood plasma being dispensed to downstream liquid handling structures.

In some embodiments, there is provided a method of controlling liquid flow in a device having an upstream liquid handling structure and a downstream liquid handling structure connected to the upstream liquid handling structure. The method comprises applying a driving force to the device to dispose a volume of liquid in the device to separate a volume of gas in the upstream liquid handling structure from a volume of gas in the downstream liquid handling structure. The method further comprises increasing the driving force to reduce a gas pressure in the upstream liquid handling structure, increase the gas pressure in the downstream liquid handling structure, or both. As described above and in more detail below, increasing the driving force causes liquid flow from the upstream liquid handling structure to the downstream liquid handling structure and thereby changes the gas volume in one or both of these structures. These volume changes result in corresponding pressure changes which can be used to control the flow of the liquid itself and/or to control pressure and liquid flows in other parts of the device.

In some embodiments, the method comprises increasing the driving force to cause liquid to flow from the upstream liquid handling structure to the downstream liquid handling structure. Subsequent to dispensing liquid from the upstream liquid handling structure to the downstream liquid handling structure, the method may include decreasing the driving force to cause gas to flow from the downstream liquid handling structure to the upstream liquid handling structure to reduce a pressure differential between the upstream liquid handling structure and the downstream liquid handling structure. This, in effect, can reset the pressure conditions in the system, thereby allowing the new dispensing of liquid without having to overcome increasingly larger pressure differentials.

In some embodiments, the method comprises using a change in gas pressure in the upstream liquid handling structure, the downstream liquid handling structure, or both to drive a flow of liquid in the respective liquid handling structure(s).

The method may comprise repeatedly increasing and decreasing the driving force to repeatedly dispense a volume of liquid from the upstream liquid handling structure to the downstream liquid handling structure.

In some embodiments, the method comprises separating the volume of liquid into fractions of different respective density by application of the driving force prior to increasing the driving force to cause liquid to flow from the upstream liquid handling structure to the downstream liquid handling structure. Subsequent to this separation, a first fraction is retained in the upstream liquid handling structure and a second fraction flows downstream. In some particular embodiments, a device as described above having liquid handling structure with a portion radially outward of the outlet port is used by rotating the device to collect a first fraction of a liquid in the liquid holding chamber in the portion. Subsequently the rotational frequency of the device is increased to dispense a second fraction of the liquid from the liquid holding chamber while retaining the first fraction in the portion. As described above, the liquid may comprise a blood sample, in which case the first fraction may comprise cellular material and a second fraction may comprise blood plasma.

In some embodiments, a fluid flow control system comprises at least a first and second volume of gas separated by at least one liquid element; wherein at least one of the first or second volume of gas is isolated from an exterior gas pressure; and means for applying a force to the liquid element or to the fluid flow control system, wherein the pressure of the volume of gas is insensitive to the force; wherein the response of the liquid element to the force changes the gas pressure difference between the first and second volume of gas, enabling a change of flow in at least one liquid element of the fluid flow control system.

In some aspects of the fluid flow control system, at least a liquid starts to flow when the force is applied to the liquid or to the system and then after a certain time stops flowing without changes in the applied force to the liquid or to the system.

In some aspects of the fluid flow control system, the liquid flow changes are used for dosing of predefined amounts of at least one liquid in the system.

In some aspects of the fluid flow control system, the liquid flow changes are used for liquid switching of at least one liquid in the system.

In some aspects of the fluid flow control system, the liquid flow changes are used for dosing of predefined amounts of at least one liquid in the system.

In some aspects of the fluid flow control system, the liquid flow changes are used for liquid pumping of at least one liquid in the system.

In some aspects, the fluid flow control system at least a second liquid is contained in the system, wherein the flow of the first liquid leads to the movement of a second liquid in the system.

In some aspects of the fluid flow control system, the liquid flow changes are used for phase or particulate separation of least one liquid in the system.

In some aspects of the fluid flow control system, the applied force is gravity.

In some aspects of the fluid flow control system, the applied force is centrifugation.

In some aspects of the fluid flow control system, the applied force is electricity.

In some aspects, the fluid flow control system includes detection elements for qualitative or quantitative determination of substances or events.

In some aspects, the fluid flow control system is operated in such a way that enables the implementation in cycles of the liquid dosing, switching, pumping or any other fluidic function obtained from an implementation of the fluid flow control system.

In some aspects, the fluid flow control system is used for blood plasma separation.

In some embodiments, there is provided a device for handling liquid, the device being rotatable about an axis of rotation to drive liquid flow within the device. The device comprises an inlet chamber having an inlet port and an outlet port connected to a respective outlet conduit defining a path downstream (radially outward) of the inlet chamber. The outlet conduit connects to other structures such as, for example, a receiving chamber. In operation, a volume of liquid is introduced to the inlet chamber via the inlet port which is subsequently sealed. Under rotation the liquid experiences a centrifugal force and moves outwards reaching the outlet, at which moment the gas contained in the inlet chamber (with volume equal to that of the chamber minus the volume of liquid introduced) is trapped within the chamber as the inlet port has been sealed and the outlet is now plugged with liquid. By increasing the rotational frequency, the liquid experiences an increasingly higher pressure difference (which scales with the square of the rotational frequency) and at a given rotational frequency this pressure difference in the liquid is larger than the pressure difference required to change the gas volume (with the corresponding decrease in absolute gas pressure inside the inlet chamber), and a given amount of liquid (or dose) is expelled through the outlet conduit to the receiving chamber. The amount of liquid expelled through the outlet conduit is a function of the increase in rotational speed, the rate at which this increase takes place, the initial volume of air trapped in the inlet chamber, and the structure position relative to the axis of rotation, geometry and dimensions.

Thus a structure is provided that once filled with a given volume of liquid and subsequently sealed, is capable of delivering a small amount of liquid by controlling the rotational frequency of the device. Further, by decreasing the rotational frequency the pressure difference in the liquid decreases and the difference in gas pressure between the gas entrapped in the inlet chamber and the remaining gas in the device is essentially constant. At a sufficiently low rotational frequency the difference in gas pressure is sufficiently high compared to the difference in liquid pressure and a gas bubble is ingested through the liquid to the inlet chamber diminishing the gas pressure difference (or increasing the absolute gas pressure entrapped inside the inlet chamber). Once the gas pressure difference has been decreased it is possible to expel again a given amount of liquid using an increase in rotational frequency as outlined above. Repeated cycles of this frequency protocol will allow ejecting a small amount of liquid every cycle, and this can be used to partially or totally empty the inlet chamber depending on the requirements of the application. The fact that a threshold rotational frequency is required to eject further liquid, allows conducting other operations in the device below this frequency, while the remaining liquid is retained in the inlet chamber. Essentially, in this case the structure operates as a switch in which no further liquid is drawn from the inlet chamber until the rotational frequency is increased above the threshold level.

In some embodiments, partial emptying of the inlet chamber by controlling the rotation of the device, i.e., the number of cycles and amplitude of rotational frequency oscillations, is used for delivering controlled amounts of liquid for downstream operations such as, for example, mixing and diluting. This provides the opportunity for having software controllable devices in which, the amount of liquid delivered is tuned either by user request or on the basis of a preliminary read-out from the device which feeds back, according to a predefined algorithm, into a rotation control unit to subsequently deliver a given amount of liquid. This approach can be used until the inlet chamber has emptied, and if required liquid can be reloaded and the chamber sealed to operate in the same fashion.

In some embodiments there is provided a device for handling liquid, the device being rotatable about an axis of rotation to drive liquid flow within the device. The device operates as described above but with the purpose to separate multi-phase fluids, such as liquid suspensions and emulsions. In this case the inlet chamber is designed with an outermost aspect which is farther from the centre of rotation than the chamber outlet connecting to the outlet conduit. In such circumstances the volume of liquid radially outwards from the radial position of the outlet, is retained in the inlet chamber. Thus it is possible to spin the device at a rotational frequency at which no liquid is transferred downstream to allow for sedimentation based separation of heavier fractions. Once sedimentation has been accomplished, repeated cycling of the device will resume dosing until the desired volume of the lighter separated fractions has been expelled. An application of such embodiments (or any of those described herein) is the separation of plasma from whole blood samples as required for many diagnostic assays.

Embodiments of the invention include micro fluidic devices which, in some embodiments, may be substantially disc shaped and in some embodiments have an axis of rotation that is defined by a feature of the device for engaging a drive mechanism for rotating the device.

Devices as described herein which control liquid flow within the device by rotation of the device are generally termed centrifugal micro fluidic devices. In cases where the device thickness is substantially smaller than the device diameter they are commonly referred to as "lab on a disc" devices; these concepts are used interchangeably herein. For the avoidance of doubt the term "dosing" refers to delivery of a given amount of liquid, "metering" refers to measuring a defined amount of liquid, and "aliquoting" refers to liquid distribution or partition in desired volumes and holding these volumes of liquid such that they are controllably releasable for later use. The term "chamber" is used in a broad sense to designate a liquid retaining structure of a given volume capacity.

Where the term "level" is used in relation to a chamber or other liquid containing structure, it will be understood that this does not necessarily refer to a straight level as would be observed in a chamber filled with liquid under gravity, but that the term includes curved levels which may be curved due to a centrifugal force acting on the liquid or due to surface tension effects, as long as this corresponds to a well-defined amount of liquid in the liquid containing structure. The "level" is not limited to the liquid retaining chamber, but rather defines a geometric locus, e.g. relative to a centre of rotation.

Where the term "vented" or "vent" is used in relation to a chamber or other liquid retaining structure, it will be understood that this refers to the chamber or other structure being in fluidic communication with atmospheric air, outside a device of which the chamber or other structure is a part, or with a closed air circuit of the device such that a gas pressure in the chamber or other structure is kept substantially constant when volume changes of a liquid in the chamber or structure occur. A closed air circuit allows air to move around the device from regions where air is displaced to regions where a negative pressure would otherwise result, thus equilibrating pressure in the device without the need for an open connection to atmospheric air.

For the avoidance of doubt, the term "microfluidic" is referred to herein to mean devices having a fluidic element such as reservoir or a channel with at least one dimension below 1 mm. The device need not be disc shaped and, indeed, the axis of rotation need not be provided within the device itself, but the device can be arranged to be placed in the rotor for rotating it about an axis of rotation not within the device itself.

BRIEF DESCRIPTION OF THE DRAWINGS

The following description of specific embodiments is made by way of example and illustration, and not limitation, with reference to the drawings, in which.

DETAILED DESCRIPTION OF FIGURES

At a general level the balance of interactions between (i) forces applied to a system and acting on a liquid but not affecting a gas pressure of at least a part of a gas volume, resulting in changes of flow behaviour in at least one liquid element of the system, and (ii) the change of gas pressure due to the change in flow behaviour of at least one of the liquid elements of the system can be exploited to control flow behavior in the system. Some liquid handling systems or processes or devices described below have an initial stable state in terms of liquid flow, then when applying forces as described in (i) above the system enters a transient state wherein liquid flow changes from its previous stable state and the change of liquid flow results in a change of gas pressure described in (ii) above, leading to a new stable state in terms of liquid flow behavior.

Figure 1A:
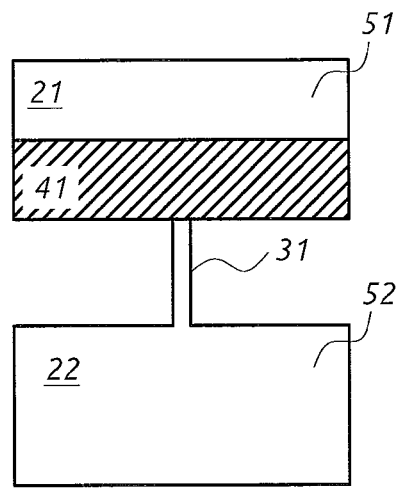
FIGS. 1A-C illustrate a basic mechanism of gas/liquid interaction in some embodiments.

With reference to FIG. 1A a liquid handling system 10 comprises a first chamber 21 containing a liquid 41 and a gas volume 51, a channel 31 connecting the first chamber 21 to a second chamber 22 containing a gas volume 52. The system 10 is in a stationary condition, in a first simple example when the liquid 41 is not flowing from the first chamber 21 into the second chamber 22. The pressure difference between the gas volumes 51 and 52 may be zero or non-zero, since the described principle is not limited to any particular configuration of initial gas pressures.

Figure 1B:
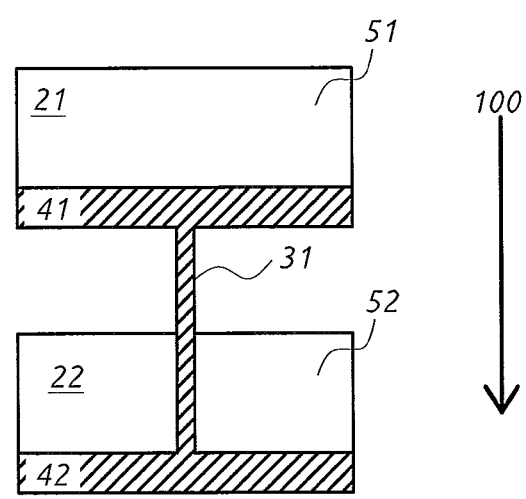

FIG. 1B represents the system 10 with a force 100 applied to the liquid 41, and having no significant effect (or at least a significantly lesser effect) on the gas volumes 51 and 52. The action of the force 100 will cause the liquid 41 to flow through the channel 31 into the chamber 22. If at least one of the gas volumes is fixed (the corresponding chamber being sealed from external atmosphere and the other chamber), the liquid movement will cause a change of pressure in each fixed gas volume, gas volume 51, gas volume 52 or both. In one configuration, both gas volumes are fixed so that the pressure of gas volume 51 decreases from p0 to p1, where p1 is less than p0, and the pressure of gas volume 52 increases from p0 to p2, where p2 is greater than p0. In another configuration, for example, the gas volume 51 is open to external atmosphere and therefore its pressure does not change from its initial pressure but the gas volume 52 is fixed so that its pressure will increase while the liquid is flowing. Alternatively, if the gas 52 is open to external pressure (e.g. atmosphere) then its pressure will remain unchanged and with gas volume 51 fixed, the pressure of gas volume 51 will decrease while the liquid is flowing.

In any of the configurations described above at least one of the gas volumes 51 or 52 will experience a change in pressure as the liquid 41 flows. This change in pressure leads to either a suction effect (decrease of pressure in gas volume 51) or over pressure effect (increase of pressure in gas volume 52) that will eventually lead to a significant change in the flow rate of the liquid 41 flowing from the initial chamber 21 into the channel 31 and to the chamber 22 as the driving force is increasingly balanced by the resulting pressure differential.

Figure 1C:
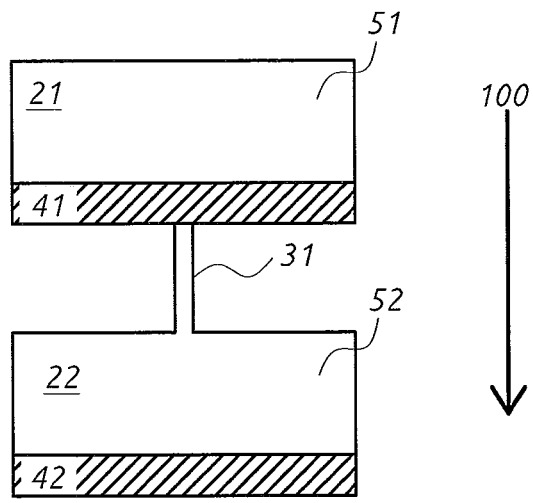

After a threshold amount of liquid related to the magnitude of the applied force 100 and to the changes in gas pressure has flowed, the flow will stop. FIG. 1C illustrates this cessation of flow while the force 100 is still being applied as the applied force is balanced by the pressure changes. From this threshold condition onwards, the system 10 will remain in a stable condition as long as the applied force is not varied. It will thus be understood that the application of the force 100 leads to a transient and non-stable state of liquid flow until the effect of the flow itself results in a balance between the forces acting on the system. From this stable condition several different effects can be achieved, depending on the system design, construction and operation.

In a first setting, if the driving force does not cause any of the liquid 41 to leave the conduit 31 into the second chamber 22, removal or reduction of the force 100 simply results in retraction of the liquid that has advanced into the conduit 31 into the first chamber 21 as the pressures return to their initial state. On the other hand, in a second setting where liquid 41 has flowed into the chamber 22 through the conduit 31 and the gas 52, the liquid will accumulate in the chamber 22 and cannot flow back to the chamber 41. In this case, a gas bubble from gas volume 52 is ingested into channel 31 to equilibrate pressures between the chambers 41 and 42 as the driving force is reduced or removed. In either case, the system will go back to a pressure state similar to the initial state if the driving force is returned to its initial state (e.g. removed). The system may thus be operated in a cyclic manner, for example having in each step of the cycle a certain amount of liquid moving from the chamber 21 into the chamber 22 to accumulate an amount of liquid 42 in the chamber 22.

Figure 2:
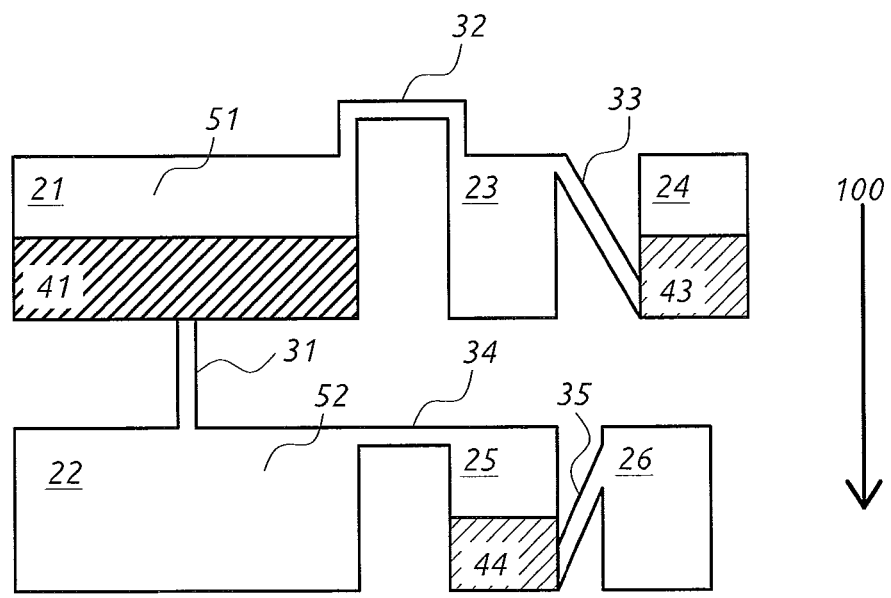
FIG. 2 illustrates an implementation with additional fluid handling functions based on the basic mechanism.

With reference to FIG. 2, by connecting further liquid handling structures to one or both of chambers 21 and 22, the pressure difference created by the flow of the liquid 41 can be used to perform additional functions in the system 10. In some such embodiments, the first chamber 21 is also connected to a channel 32, connected in turn to a chamber 23. The chamber 23 is connected via a channel 33, to another chamber 24 containing a liquid 43. In this case the gas volume 51 extends to the chamber 23 and channels 32 and 33 but not the chamber 24. As the gas volume 51 is sealed from external pressure, the process described above with reference to FIGS. 1A, 1B and 1C leads to a negative pressure suction effect in the channel 33, and causing the liquid 43 to flow into the channel 33 against the direction of the force 100 and possibly onwards. This can be used to pump volumes of the liquid 43 from its original chamber 24 into the chamber 23.

In some embodiments the second chamber 22 is connected to a channel 34, which in turn is connected to a chamber 25 containing a liquid 44. The chamber 25 is further connected to a chamber 26 by a channel 35. At rest the liquid 44 is at the bottom of the chamber 25. In this case, if the gas volume 52 is sealed from external pressure, then the process described above with reference to FIGS. 1A, 1B and 1C leads to a pressure increase in the gas volume 52 that may force the liquid 44 to move through the channel 35 into the chamber 26. Thus, pumping or dosing of the liquid 44 from its original chamber 25 into the chamber 26 can be achieved in these embodiments.

Implementations like those illustrated in FIG. 2 can be used in several applications where liquid movement is desired in multiple regions of a liquid handling system in a simple and reproducible manner. For example, chambers 23 and 25 are not necessary, since similar effects would occur if the chambers 24 and 26 are directly connected to the chamber 21 and 22, respectively. Any combination of the effects described above can be implemented, so there is no limitation with respect to the modules (suction, pumping, dosing, etc) used in the system 10.

The embodiments described above can be implemented in a variety of systems, using as a driving force, gravity, centrifugation, electricity, combinations thereof or any other force having a significant differential effect on the liquid and gas volumes in the system.

Figure 3A:
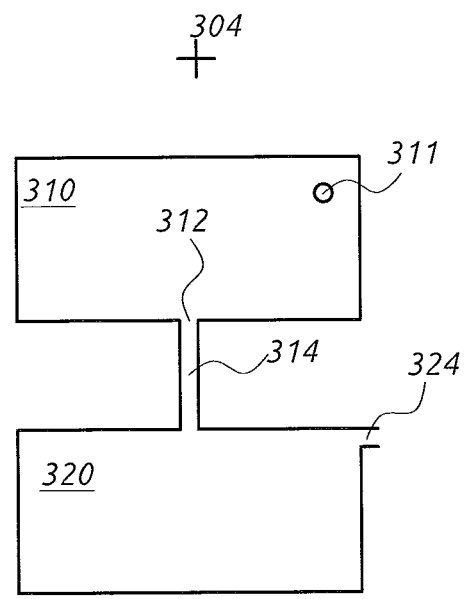
FIGS. 3A-E illustrate a rotating device embodiment and its operation.

A specific embodiment is now described with reference to FIG. 3A. A centrifugal or "lab on a disc" microfluidic device 302 arranged for rotation about an axis 304 comprises a chamber 310 having an inlet 311 and an outlet 312 connected to an outlet conduit 314 extending radially outwards from the outlet 312 and to a receiving chamber 320. The inlet 311 communicates with the outside of the device to allow liquid to be supplied to the chamber 310 and can be sealed from atmospheric air by means of an adhesive flap. In some embodiments other means for supplying liquid and sealing the inlet 311 are used. For example, the inlet 311 is, in some embodiments, fed from an internal liquid supply structure. In some embodiments, the inlet 311 can be sealed by means of a phase change material. Other embodiments employ external liquid supply structures which are coupled to the device and ruptured at the time of use, for example liquid storage container such as a blister pack.

The chamber 310 is only vented through the inlet port 311 and the outlet port 312 and the chamber 320 is vented through the vent port 324.

A given liquid 330 is introduced to chamber 310 via the inlet 311, for example by applying a drop of liquid to the inlet 311 from the outer surface of the device 302. The chamber 310 is subsequently sealed from atmospheric air at which point all gas contained in the system is at atmospheric pressure, p0.

Figure 3B:
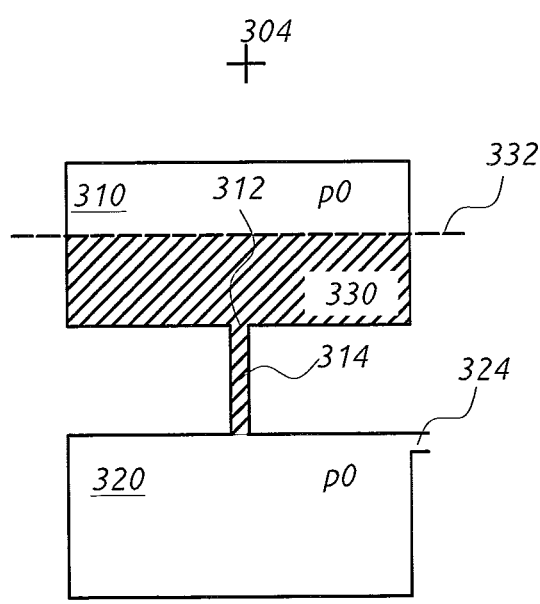

With reference to FIG. 3B, rotation of the device 302 around the axis 304 will drive the liquid 330 outwards until it reaches outlet 312 at which moment the gas contained in chamber 310 cannot escape as inlet 311 has been sealed and outlet 312 is now plugged with liquid experiencing a liquid head due to the centrifugal force. At a given rotational frequency, liquid escapes through the outlet 312 into the outlet conduit 314. As liquid escapes through the outlet 312 the volume of confined gas increases and consequently there is a decrease in the absolute pressure of the gas confined in the chamber 310. This decrease in absolute gas pressure in the chamber 310 results in a gas pressure difference between chamber 310 and 320 which, after a corresponding volume of liquid has passed through the outlet 312, counterbalances the centrifugal pressure difference experienced by the liquid and flow comes to a halt with liquid 330 levelling at a radial position 332. There is thus an upper threshold frequency of rotation of the device 302, $\omega_H$, at which the gas volume change corresponding to liquid 330 completely filling the outlet conduit 314 results in a pressure difference between the chambers 310 and 320, which is balanced by the pressure due to the centrifugal force.

The balance established in terms of gas and centrifugal pressures can be disturbed by changing the rotational frequency as the centrifugal pressure difference scales with the square of the rotational frequency and the difference in gas pressure is mostly dependent on the gas volume increase (or liquid volume decrease) relative to the initial gas volume in the chamber 310 and independent of the changes in rotational frequency.

Figure 3C:
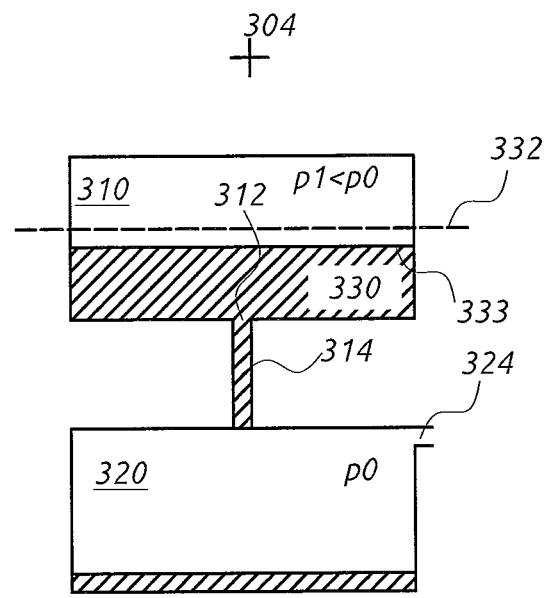

With reference to FIG. 3C, the rotational frequency is increased beyond the upper threshold frequency $\omega_H$ and the centrifugal pressure difference experienced by the liquid increases sufficiently to eject liquid 330 to the downstream chamber 320. Consequently there is a further increase in the gas pressure difference between chambers 310 (at a pressure of p1) and 320 (at a pressure of p0, where p1 is less than p0) and flow stops again with the level of liquid in the chamber 310 now being at a radial position 333, at which point the system reaches a new balance between liquid and gas pressure differences. The amount of liquid 330 ejected is thus determined by the increase in rotational frequency beyond the upper rotation frequency threshold $\omega_H$.

Figure 3D:
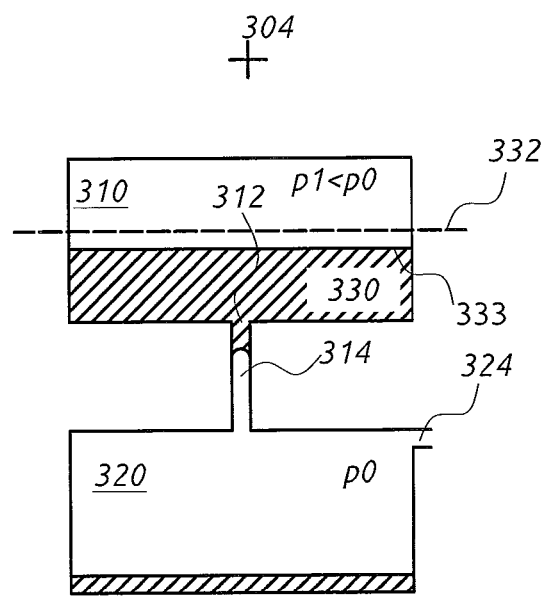
Figure 3E:
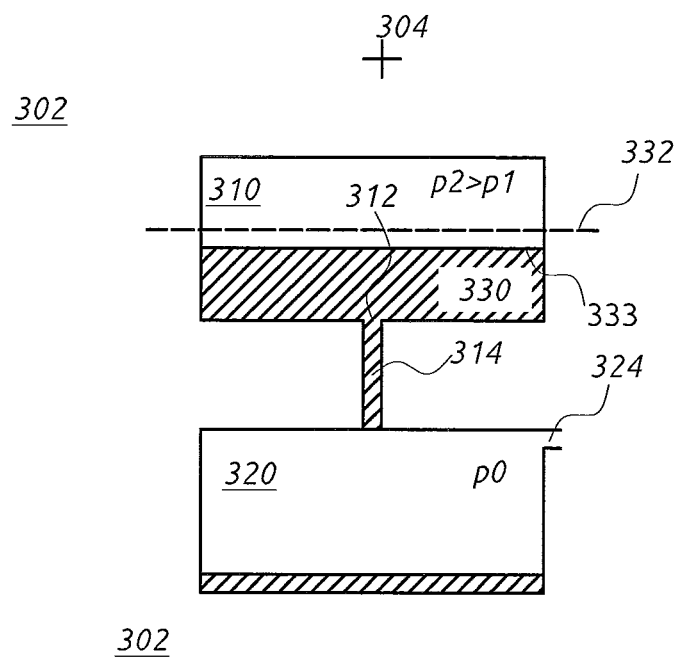

At some stage, however, ejecting further amounts of liquid (further dosing) by rotational frequency adjustments will require the use of increasing rotational frequencies which are impractical to achieve, or require additional complexity of the driving unit and centrifugal device with regard to stability, flatness and robustness. With reference to FIG. 3D, advantageously, the system can be operated for further dosing in a reliable manner by lowering the rotational frequency after the first dosing event described above with reference to FIG. 3C, to a lower threshold $\omega_L$ at which the gas pressure difference exceeds the centrifugal pressure difference and gas is ingested radially inwards through the outlet conduit 314, forming a bubble which transverses the liquid radially inwards until reaching the confined gas volume at a radially inner portion of the chamber 310 (see FIG. 3E). This increases the absolute gas pressure in the chamber 310 to a pressure of p2, where p2 is greater than p1, thereby decreasing the gas pressure difference between chambers 310 and 320. Further dosing can then be achieved with further cycles of rotational frequency as described above.

Figure 4:
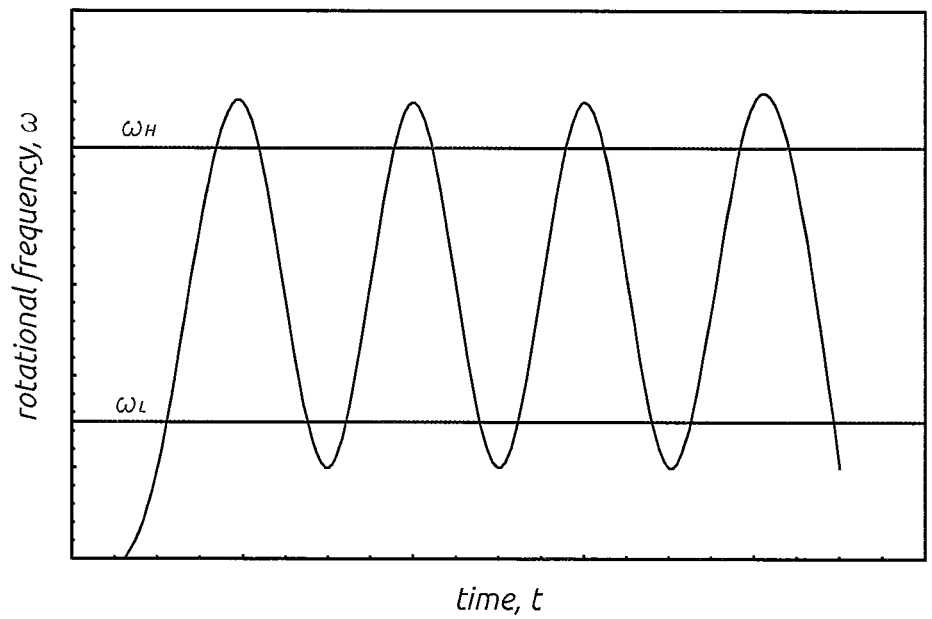
FIG. 4 depicts a rotational frequency protocol for the rotating device.

With reference to FIG. 4, a typical rotational frequency protocol for controlled dosing as described above requires that cycles of sufficient amplitude are used to cover both the upper $\omega_H$ and lower $\omega_L$ threshold rotational frequencies for, respectively, expelling liquid to the chamber 320 and ingesting a bubble back into the chamber 310. Each cycle releases an amount of liquid which is a function of the increase in rotational speed, the rate at which this increase takes place, the initial volume of air trapped in the inlet chamber (volume of the inlet chamber 310 minus the volume of the introduced liquid), the position relative to the axis of rotation of the structure, its geometry and dimensions. For example, to ensure reliable operation, the geometry and dimensions of the outlet conduit 314 are designed such that when liquid first starts escaping from the outlet 312 the full cross-section of the outlet conduit 314 is occupied by liquid to avoid gas exchange between the chambers 310 and 320. Typical embodiments achieve this with the outlet conduit 314 having smallest dimensions below 1 mm and preferably below 0.5 mm, (in applications handling, for example, aqueous liquids such as blood or blood plasma). In some embodiments, the outlet conduit may have a constant cross-section, although the cross-section may vary along the conduit channel in other embodiments.

Further continued cycling as described above with reference to FIG. 4, enables ejection of a liquid dose per cycle. As a consequence of liquid being transferred from the chamber 310 to the chamber 320, the level of liquid in the chamber 310 moves radially outwards and hence the liquid head (i.e. the radial extent of the liquid column) decreases and consequently the centrifugal pressure difference experienced by the liquid at a given rotational frequency decreases every cycle. This effect can be minimized by design, arranging the inlet chamber 310 such that it has a greater circumferential extent than radial extent and/or arranging the outlet conduit 314 to have significantly larger radial extent compared to the radial extent of liquid inside the chamber 310. This ensures a relatively small fractional change of liquid head until chamber 310 is emptied. Additionally it is also noteworthy that the decrease in absolute pressure of gas confined in the chamber 310 as liquid is transferred to the chamber 320 also decreases for a given liquid dose because this decrease is proportional to the ratio between the liquid dose and the gas volume prior to liquid being transferred. This effect can be minimized by ensuring that an initial gas volume in the chamber 310 is larger than the volume of liquid initially introduced into chamber 310, to reduce the percentage gas volume change as the chamber 310 empties. While the device can be designed to keep liquid head and percentage gas volume changes low over several dosing events, FIG. 4 is an idealized diagram and it is clear that the upper $\omega_H$ and lower $\omega_L$ threshold rotational frequencies change in magnitude over time for successive dosing events. However, these changes are predictable from the parameters discussed above and, in some embodiments, the rotation protocol is changed with successive dosing events (not necessarily after each dosing event) to compensate for these changes and ensure consistent dosing. Naturally, this is an optional feature in case that consistent dosing volumes are required over several cycles.

Some embodiments include further fluidic parts and structures in communication with the chamber 320 to enable further liquids to flow into the chamber 320, such as required for mixing and diluting, and/or for delivering the dosed liquids to additional downstream liquid processing structures.

The port 324 in the chamber 320 acts as a vent in order to maintain the gas pressure in chamber 320 substantially constant. However, some embodiments omit any vent port in which case the gas pressure difference between chambers would increase for a given dose compared to a vented chamber 320 as the confined gas volume in chamber 320 is reduced with each dose. This is a consequence of the decrease in absolute gas pressure in chamber 310 combined with an increase in absolute pressure of the confined gas in chamber 320. In these embodiments the threshold rotational frequencies can be adjusted to account for the change in the pressure balance.

Figure 5A:
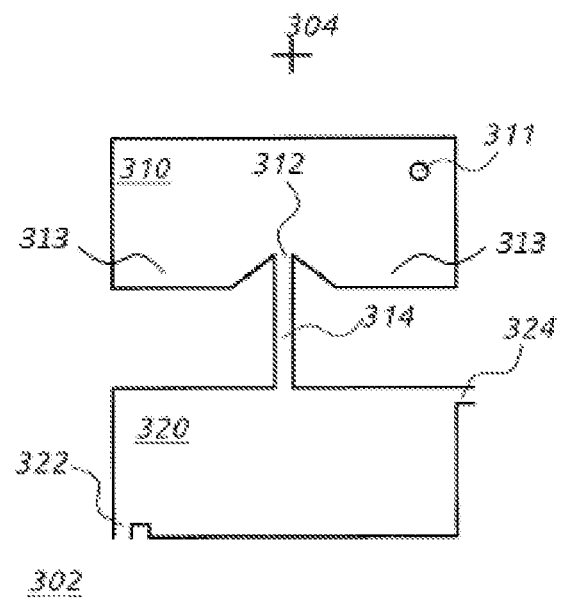
FIGS. 5A-D illustrate an embodiment with a phase separation structure in a rotating device and its operation.

In some embodiments now described with reference to FIG. 5A, the chamber 310 is arranged such that the outlet 312 is positioned radially inwards from the outermost aspects 313 of chamber 310 so that a defined volume of liquid in the chamber (the volume radially beyond outlet 312) is retained in the chamber 310. This enables a multi-phase liquid to be separated in at least two of its fractions.

In operation, a multi-phase liquid 330, for example blood, is introduced into chamber 310 via the inlet 311, which is subsequently sealed as described above. The device 302 is rotated and the multi-phase liquid 330 is driven outwards by the action of the centrifugal force field until it reaches the outlet 312 confining the gas in chamber 310 to a given volume.

Figure 5B:
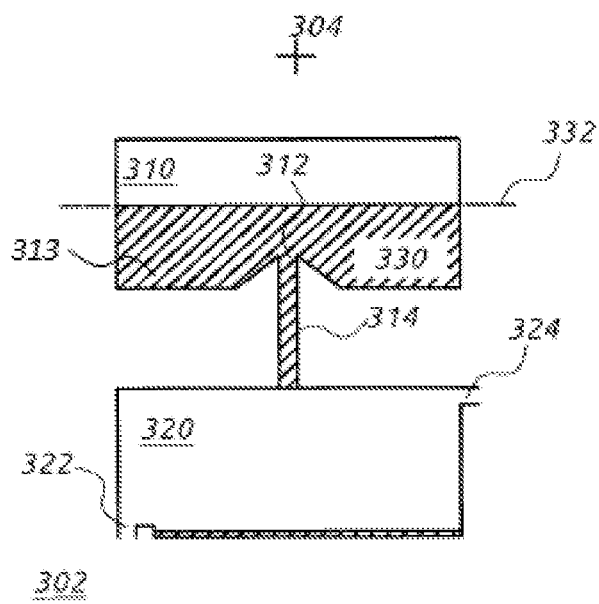

With reference to FIG. 5B, on continued rotation liquid will flow into the conduit 314 towards the chamber 320 until flow comes to a halt as a result of the balance between the gas and liquid pressure differences as explained above. Further rotation at frequencies below the upper frequency threshold $\omega_H$ (i.e. without ejecting liquid), allows the denser components 330a of the liquid 330 to sediment in the outermost aspects 313 of chamber 310 under the influence of the centrifugal force.

Figure 5C:
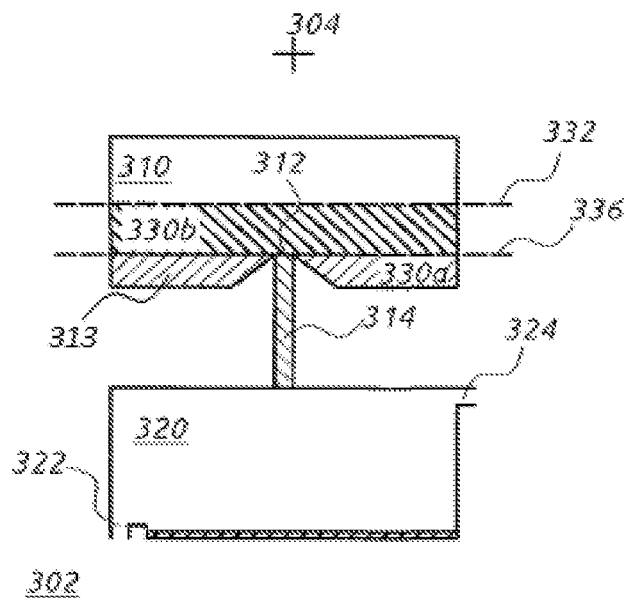
Figure 5D:
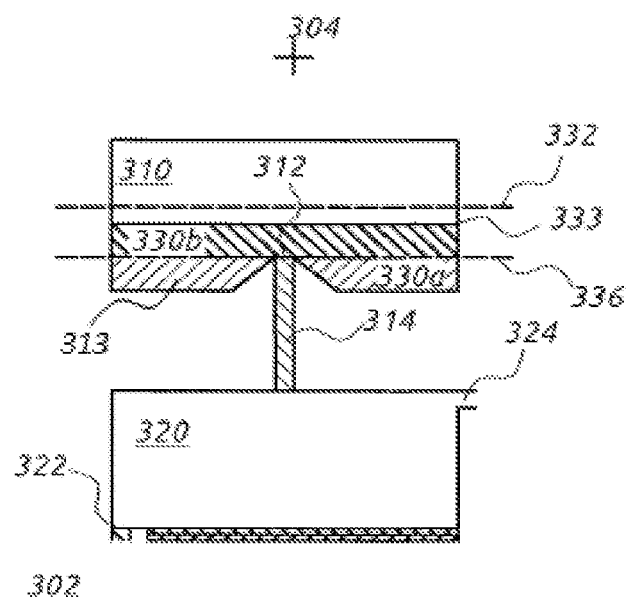

With reference to FIG. 5C, an interface 336 thus forms between phases 330a and 330b of the multi-phase liquid 330. The chamber 310 is arranged such that for a predefined initial volume of multi-phase liquid 330, only the volume of the lighter phase(s) 330b is located radially inwards of the outlet 312 after sedimentation is complete. From this moment, the device can be cycled as illustrated in FIG. 4 in order to repeatedly expel doses of the separated lighter phase(s) 330b. The receiving chamber 320 has an outlet 322 which is positioned radially inwards from the outermost aspects 313 of the chamber 320 in order to retain eventual denser phase(s) 330a that may have escaped during the first spin of the device prior to the sedimentation phase. Thus any escaped volumes of the denser phase(s) 330a is substantially retained in the outermost aspects 313 of the chamber 320 and only subsequently separated lighter phase(s) 330b will escape through the outlet 322 for further downstream operations, as illustrated in FIG. 5D.

Microfluidic devices as described above are, in some embodiments, fabricated by standard lithographic procedures. One approach is the use of photo-resist material of different thickness to obtain multiple depth structures. These films are applied by spin coating or lamination of dry-films on flat substrates such as transparent polymeric disc shaped substrates. After developing and etching the structures, disc substrates are aligned and bonded by the application of temperature and pressure. The substrates are provided with fluidic connections such as inlet and outlet ports by punching, milling or laser ablation. Specifically, the devices described above have, in some embodiments, reservoir (e.g. chambers) and conduit depths of, respectively, 100 and 50 micrometers. Other manufacturing techniques are used in some embodiments and include direct laser ablation, computer numerically controlled (CNC) milling, hot embossing, injection molding or injection/compression molding of PMMA (polymethyl methacrylate), PC (polycarbonate), PS (polystyrene), COP and COC (cyclocolefin polymers and co-polymers).

After forming the fluid handling structure on one substrate, typically a next step is required to confine the fluid handling structure using a second substrate or film. Bonding of polymeric materials can be achieved by a variety of means including the use of adhesion promoting materials (e.g. liquid glues, solid adhesives, radiation curing, laser bonding, catalyst assisted bonding, solvent assisted bonding or thermally activated adhesion promoters), or through direct application of temperature provided there is intimate contact of the bonding surfaces. In particular, the microfluidic structures may be produced in one or both of two clear substrates, one clear and one darkly pigmented substrate or two darkly pigmented substrates depending on the analysis and detection applications performed subsequently to the microfluidic processing.

As described above, in some embodiments fluid handling structures such as an air (vent) circuit are formed in the second (cover) substrate or film or in an intermediate substrate or film bonded between outer layers of the device.

Figure 6:
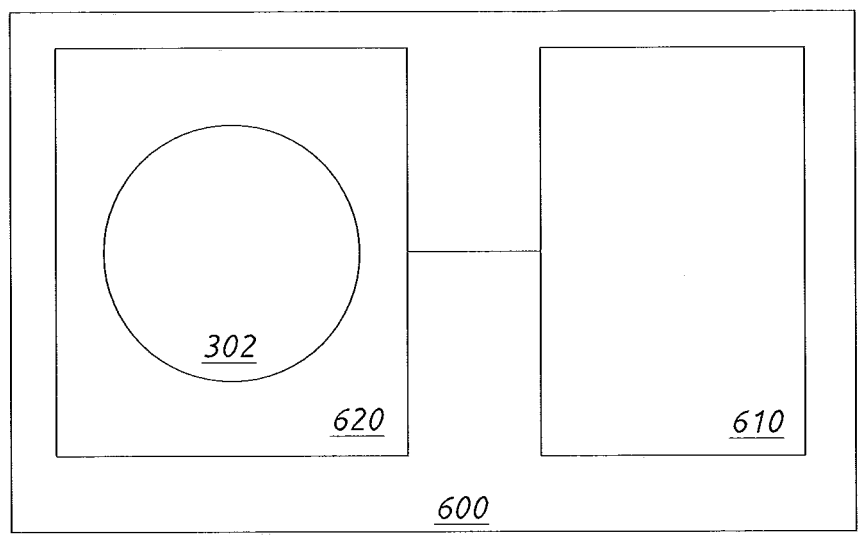
FIG. 6 illustrates a drive system.

With reference to FIG. 6, a drive system 600 for driving a device as described above comprises a controller 610. The controller is arranged to control a drive 620 for driving the device to create the driving force for driving liquid flow in the system 10 or device 302, as described above. Where the driving force is a centrifugal force as in the case of the device 302, the controller 610 controls a motor in the drive 620 driving a spindle to which the device 302 can be attached for rotating the device to create the centrifugal force. Naturally, as discussed above, other driving forces are also applicable and the drive system 600, controller 610 and drive 620 are adapted accordingly, for example to provide a gravitational or electric driving force.

The above description of detailed embodiments of the invention is made by way of illustration and not for the purpose of limitation. In particular, many alterations, modifications, combinations and juxtapositions of the features described above will occur to the person skilled in the art and form part of the invention.

The invention claimed is:

1. A method of controlling liquid flow in a device having an upstream liquid handling structure comprising an outlet port and a downstream liquid handling structure connected to the upstream liquid handling structure through the outlet port, the method comprising:
   applying a driving force to the device to dispose a volume of liquid in the device to separate a volume of gas in the upstream liquid handling structure from a volume of gas in the downstream liquid handling structure;
   increasing the driving force to cause liquid to flow from the upstream liquid handling structure to the downstream liquid handling structure through the outlet port to reduce a gas pressure in the upstream liquid handling structure, increase a gas pressure in the downstream liquid handling structure, or both and
   subsequent to dispensing liquid from the upstream liquid handling structure to the downstream liquid handling structure, decreasing the driving force to cause gas to flow from the downstream liquid handling structure to the upstream liquid handling structure through the outlet port to reduce a gas pressure differential between the upstream liquid handling structure and the downstream liquid handling structure.

2. A method as claimed in claim 1, the method comprising using a change in gas pressure in the upstream liquid handling structure, the downstream liquid handling structure, or both to drive a flow of liquid in the respective liquid handling structure or structures.

3. A method as claimed in claim 1, the method comprising repeatedly increasing and decreasing the driving force to repeatedly dispense a volume of liquid from the upstream liquid handling structure to the downstream liquid handling structure.

4. A method as claimed in claim 1, the method comprising separating the volume of liquid into fractions of different respective density by application of the driving force prior to increasing the driving force to cause liquid to flow from the upstream liquid handling structure to the downstream liquid handling structure and, subsequently, retaining at least one of the fractions in the upstream liquid handling structure.

5. A method as claimed in claim 4, wherein the liquid includes a blood sample.

* * * * *